United States Patent

Yokomichi et al.

[11] Patent Number: 5,514,405
[45] Date of Patent: May 7, 1996

[54] FRYING OIL OR FAT COMPOSITION

[75] Inventors: Hideki Yokomichi; Yuji Okauchi; Takeshi Oka; Koichi Okisaka; Hirokazu Kokumai; Shin Koike; Kenta Mori, all of Ibaraki; Mika Tabeta, Chiba, all of Japan

[73] Assignee: Kao Corporation, Tokyo, Japan

[21] Appl. No.: 530,015

[22] Filed: Sep. 19, 1995

Related U.S. Application Data

[63] Continuation of Ser. No. 114,003, Aug. 30, 1993, abandoned.

[30] Foreign Application Priority Data

Jun. 30, 1993 [JP] Japan ..................... 5-187229

[51] Int. Cl.$^6$ ..................................... A23D 7/005
[52] U.S. Cl. ..................... 426/604; 426/611; 426/804; 426/438
[58] Field of Search ..................... 426/604, 611, 426/804, 438

[56] References Cited

U.S. PATENT DOCUMENTS

| | | | |
|---|---|---|---|
| 3,914,458 | 10/1975 | Terada | 426/604 |
| 4,840,815 | 6/1989 | Meyer | 426/804 |
| 4,940,601 | 7/1990 | Orphanos | 426/611 |
| 5,009,904 | 4/1991 | Saslaw | 426/438 |
| 5,017,398 | 5/1991 | Jandacek | 426/604 |
| 5,021,256 | 6/1991 | Guffey | 426/804 |
| 5,063,076 | 11/1991 | Finlayson | 426/604 |
| 5,176,933 | 1/1993 | Fulcher | 426/438 |
| 5,236,733 | 8/1993 | Zimmerman | 426/804 |
| 5,264,237 | 11/1993 | Traitler | 426/804 |
| 5,294,451 | 3/1994 | Meyer | 426/804 |

*Primary Examiner*—Carolyn Paden
*Attorney, Agent, or Firm*—McAulay Fisher Nissen Goldberg & Kiel

[57] ABSTRACT

A frying oil or fat composition employable for producing fried foodstuffs having satisfactory crisp and well acceptable moderate oily or fatty taste comprises not more than 4.0 weight % of an emulsifier dissolved in an oil or a fat. The emulsifier should be chosen to make the oil or fat composition show an interfacial tension of not more than 7 mN/m at 80° C., 3 sec. after the time when the oil or fat composition is mixed with water to form an interface between a phase of the oil or fat and an aqueous phase. A frying oil or fat composition containing a sugar fatty acid ester of a specifically selected composition, or a combination of a sugar fatty acid ester and a polyglycerol fatty acid ester and/or a diglyceride is also employable for the same purpose.

14 Claims, No Drawings

FRYING OIL OR FAT COMPOSITION

This is a continuation of application Ser. No. 08/114,003, filed Aug. 30, 1993, now abandoned.

BACKGROUND OF THE INVENTION

1. Field of Invention

The present invention relates to a frying oil or fat composition for use to fry therein foodstuffs such as meats, fishes, shellfishes, and vegetables. Particularly, the invention relates to a frying oil or fat composition which is suitably employed to prepare a deeply fried foodstuffs having favorable appearance, taste and crisp.

2. Description of Prior Art

The frying oil or fat composition (hereinafter, simply referred to as "flying oil composition" or "frying oil") is employed as heating medium for cooking foodstuffs on frying pans, frying pots, cooking plates, or the like, and also for keeping the cooked foodstuffs from the frying pans and the like. Further, the frying oil or fat composition is used to impart to the cooked foodstuffs favorable taste and crisp. For example, the so called "Tempura" (Japanese deep-fat fried fish) and other fried foodstuffs are cooked using a liquid oil or a fat such as corn oil, soybean oil, rapeseed oil, cottonseed oil, rice bran oil, safflower oil, high-oleic safflower oil, sunflower oil, high-oleic sunflower oil, sesame oil, olive oil, palm oil, or lard, singly or in combination of one or more of these oils or fats. It is known that fried foodstuffs such as Tempura having favorable appearance, taste and crisp are not easily produced without trained skill. For instance, highly trained skill is required to appropriately choose the oil or fat, mixing ratio of oils and fats, frying temperature and frying period. Further, high skill is required to deal with the foodstuffs in the frying oils. The fried foodstuffs produced by those having poor skill give poor appearance (for example, lack of flowery coating, particularly for Tempura), mal odor or smell due to oxidation of the employed oil by heating under inappropriate conditions, unfavorably oily taste and poor crisp.

Heretofore, the following procedures have been generally adopted for obtaining favorably fried foodstuffs:

(1) In order to obviate excessively oily taste, the content of gluten in the wheat flour to be employed for coating the foodstuffs is reduced; flour concentration in the aqueous flour mixture (dough) for the preparation of the coating is reduced; and the aqueous flour mixture is produced using chilled water to suppress production of gluten in the flour;

(2) In order to impart to the fried foodstuffs favorable crisp, the foodstuffs are continuously moved or swayed in the frying oil to extend the oil uniformly within the coating; and the frying procedure is performed in a frying oil at a higher temperature so as to quickly evaporate a great amount of water from the coating; and (3) In order to reduce oxidation or deterioration of the frying oil as well as to obviate excessively oily taste, an anti-oxidant is incorporated into the frying oils. Unfavorable effects given by oxidation of oils are reported in J. Nutrition, 90, 199 (1960) and other publications. As antioxidants, BHA and TBA are employed. Further, a silicone oil is added to the frying oil to keep the oil from atmospheric oxygen. Recently, antioxidants of natural origin such as lecithin, tocopherol and extracts of coffee and tea are used.

The frying oil or fat preferably is in the form of liquid at room temperature. Japanese Patent Provisional Publications No. 47(1972)-34,703, No. 63(1988)-79,560 and No. 63(1988)-63,343 describe that nonionic surface active agents of polyalcohol type having a high esterification percentage (namely, having esterification percentage of not less than 80%, and low HLB) which are able to keep the oil from formation of crystalline structure therein, or that an oil portion which easily crystallizes at low temperatures is removed by means of wintering.

SUMMARY OF THE INVENTION

An object of the present invention is to provide a new frying oil and/or fat composition having improved characteristics.

Specifically, the object of the invention is to provide a frying oil or fat composition having the following favorable characteristics:

(1) production of improved flowery coating over the fried foodstuffs;

(2) improvement of crisp of the fried foodstuffs by accelerating a rate of water evaporation from the coating of the foodstuffs in the frying procedure;

(3) reduced oil spattering in the frying procedure;

(4) reduced real odor (i.e., burning semll) caused by oxidation of heated oil or fat in the frying procedure;

(5) less deterioration of heated oil or fat used in the frying procedure; and (6) improved storage stability, particularly, at low temperatures.

The present invention resides in a frying oil or fat composition comprising not more than 4.0 weight % (preferably not more than 3.0 weight %, more preferably not more than 2.0 weight %) of an emulsifier dissolved in an oil or a fat, said emulsifier being selected to make the oil or fat composition show an interfacial tension of not more than 7 mN/m (preferably not more than 5 mN/m, more preferably not more than 3 mN/m) at 80° C., 8 seconds after the time when the oil or fat composition is mixed with water to form an interface between the resulting oil or fat phase and an aqueous phase.

Moreover, the emulsifier is preferably selected to make the oil or fat composition show an interfacial tension of not more than 5 mN/m (particularly, not more than 3 mN/m) at 80° C. at 5 seconds after the formation of the interface.

The temperature 80° C. for the measurement of the interfacial tension is determined because the temperature observed when foodstuffs having an aqueous flour paste coating thereover are added in a heated oil or fat is approximately 80° C. around the interface between the heated oil or fat and the coating in ordinary frying procedures.

The above emulsifier is preferably selected from the group consisting of sorbitol fatty acid esters, sorbitan fatty acid esters, polyglycerol fatty acid esters, alkylglucosides, erythritol fatty acid esters, and polyoxyethylenesorbitan fatty acid esters. Another preferred emulsifier is a sugar fatty acid ester. More preferably, the emulsifier comprises a combination of a sugar fatty acid ester and a polyalcohol type nonionic surfactant selected from the group consisting of sorbitol fatty acid esters, sorbitan fatty acid esters, alkylglucosides, erythritol fatty acid esters, and polyoxyethylenesorbitan fatty acid esters.

The invention also resides in a frying oil or fat composition comprising a major portion of an oil or a fat, 0.01–5 weight % of a sugar fatty acid ester, and 0.01–5 weight % of a polyglycerol fatty acid ester.

This frying oil or fag composition preferably further contains 5–50 weight % of a diglyceride (weight % is based on the total amount of the oil or fat composition).

The sugar fatty acid ester preferably comprises at least 20 weight % of a sugar fatty acid diester and 15–75 weight % (more preferably 15–45 weight %) of a sugar fatty acid triester. Further, the sugar fatty acid ester preferably contains not more than 10 weight % of a sugar fatty acid monoester, and the polyglycerol fatty acid ester preferably has an esterification percentage in the range of 20% to 75%.

The invention further resides in a frying oil or fat composition comprising a major portion of an oil or a fat, 0.01–5 weight % of a sugar fatty acid ester, and 5–50 weight % of a diglyceride.

In this frying oil or fat composition, the sugar fatty acid ester preferably comprises at least 20 weight % of a sugar fatty acid diester and 15–45 weight % of a sugar fatty acid triester. Further, the sugar fatty acid ester preferably contains not more than 10 weight % of a sugar fatty acid monoester, and the diglyceride has fatty acid moieties, in which at least 70 weight % of the fatty acid moieties are unsaturated fatty acid moieties.

The invention furthermore resides in a frying oil or fat composition comprising a major portion of an oil or a fat and 0.01–5 weight % of a sugar fatty acid ester, in which the sugar fatty acid ester comprises a sugar fatty acid monoester, a sugar fatty acid diester, a sugar fatty acid triester, and a sugar fatty acid polyester comprising its tetra or higher esters, under the following conditions:

$2 \leq$ mean esterification value $\leq 4.5$ $([SPE]+[STE])/[SDE] \leq 2.3$ $[SME]/[SDE] \leq 0.1$ $[SPE]/[SDE] \leq 0.8$ wherein [SME], [SDE], [STE], and [SPE] mean amounts of the sugar fatty acid monoester, sugar fatty acid diester, sugar fatty acid triester, and sugar fatty acid polyester, respectively, comprised in the sugar fatty acid ester.

The esterification value means number of fatty acid moieties attached to one sugar moiety of the sugar fatty acid ester.

The mean esterification value is defined by the following equation:

$$\text{Mean esterification value} = \sum_{i=1}^{8} (i \times Wi/100)$$

wherein "Wi" stands for weight % of sugar fatty acid ester having a esterification value of "i".

In the above frying oil or fat composition, the sugar fatty acid ester preferably has fatty acid moieties, in which at least 50 weight % (more preferably, at least 70 weight %, most preferably at least 90 weight %) of the fatty acid moieties are unsaturated fatty acid moieties.

Further, the monoester, diester, triester and polyester preferably satisfy the following conditions:

5 wt. % $\leq [SPE] \leq 25$ wt. %

$([SPE]+[STE])/[SDE] \leq 2.0$ $2.0 \leq$ mean esterification value $\leq 3.5$ $[SME]/[SDE] \leq 0.05$ $[SPE]/[SDE] \leq 0.7$ 25 wt. % $\leq [SDE] \leq 90$ wt. %

DETAILED DESCRIPTION OF THE INVENTION

In one aspect, the present invention is based on the finding by the present inventors, that is, fried foodstuffs having satisfactory crisp and well acceptable moderate oily or fatty taste can be obtained by rapidly extending or spreading the frying oil or fat into the coating of the foodstuffs at the intial stage of the frying procedure by means of lowering an interfacial tension between the coating layer and the oil or fat phase. Such quick lowering of the interfacial tension between the coating layer and the oil or fat phase can be accomplished by the addition of a specifically selected emulsifier to the frying oil or fat. Further, the present inventors have found that the addition of such specific emulsifier to the frying oil or fat is effective not only to reduce degradation and spattering of the oil or fat in the heating procedure, but also to quickly separate an excessive frying oil or fat from the fried foodstuffs.

There are no specific limitations with respect to the oil or fat to be employed in the frying oil or fat compositions according to the present invention. Oils and fats which are conventionally employed for frying foodstuffs can be employed. Examples of the oils and fats include corn oil, soybean oil, rapeseed oil, cottonseed oil, rice bran oil, safflower oil, high-oleic safflower oil, sunflower oil, high-oleic sunflower oil, sesame oil, olive oil, palm oil, and lard (deodorized, and hydrogenated). These oils and fats can be employed singly or in combination of one or more of these oils or fats.

The emulsifiers which are favorably employable for quickly lowering the interfacial tension between the coating of the foodstuffs and the oil or fat in the frying procedure are preferably selected from polyalcohol-type nonionic surfactants such as sorbitol fatty acid esters, sorbitan fatty acid esters, polyglycerol fatty acid esters, alkylglucosides, erythritol fatty acid esters, and polyoxyethylenesorbitan fatty acid esters. It should be noted that not all these emulsifiers can be employed for producing the well acceptable fried foodstuffs. These polyalcohol-type nonionic surfactants can be employed in the invention, provided that they can serve in the frying oil or fat composition to quickly form the desired low interfacial tension between the coating layer of the foodstuffs and the oil or fat phase, when they are used in an amount of not more than 4.0 weight %. For instance, polyalcohol-type nonionic surfactants having a high esterification percentage (degree of esterification) such as higher than 80% are not able to quickly form the desired low interfacial tension. Therefore, they are not appropriate for the use in the above invention.

A sugar fatty acid ester is also preferably employable, so long as it can serve in the frying oil or fat composition to quickly form the low interfacial tension between the coating layer of the foodstuffs and the oil or fat phase, when it is used in an amount of not more than 4.0 weight %.

A combination of a sugar fatty acid ester and one or more of the polyalcohol-type nonionic surfactants are also preferably employed. In the case of utilizing such combination, the amount of emulsifier required to give the desired interfacial tension can be reduced. As a result, the taste and crisp of the fried foodstuffs are improved. Further, more well acceptable moderate oiliness can be provided to the fried foodstuffs. In this combination, each of the sugar fatty acid ester and the polyalcohol-type nonionic surfactant is preferably incorporated into an oil or a fat in an amount of not more than 1 weight % (more preferably, not more than 0.5 weight %).

The interfacial tension mentioned in the invention means "dynamic interfacial tension". Details of the dynamic interfacial tension are described in "New Lectures of Experimental Chemistry, Vol. 18, Interface and Colloid" (third edition editted by The Chemical Society of Japan, published by Maruzen, Japan, 1983). The dynamic interfacial tension can be determined using a commercially available interfacial tension measuring apparatus (for instance, Drop Volume Tensiometer-TVT1 available from LAUDA DR. R. WOBSER GMBH & CO, KG). Details of the measuring procedure are described hereinlater.

As described before, the amount of the emulsifier preferably does not exceed the 4 weight % in the frying oil or fat composition. Increase of the amount of the emulsifier in the frying oil or fat composition gives adverse effect on taste of the resulting fried foodstuffs. Accordingly, the amount of the emulsifier should be as small as possible, so long as the incorporated emulsifier can serve in the frying oil or fat composition to quickly form the low interfacial tension between the coating layer of the foodstuffs and the oil or fat phase.

More detailed descriptions of the preferably employable emulsifiers are given below.

The preferred emulsifiers are the above-mentioned esters having an esterification percentage in the range of 20% to 70% (more specifically 20% to 40%). In the description for the esters, the term of "esterification percentage" or "degree of esterification" means a ratio of number of esterified hydroxyl groups per the total hydroxyl groups (esterified and not-esterified) of the sugar or polyols which forms the esters.

The preferred esters have a relatively great amount of unsaturated fatty acid moieties, because such esters are well soluble in oils or fats, and hence are easy to handle. Therefore, the esters preferably contain unsaturated fatty acid in an amount of at least 50 weight % (more preferably at least 60 weight %) therein. Examples of the preferred unsaturated fatty acids include oleic acid, linoleic acid, linolenic acid, and their mixtures.

(1) Sorbitol fatty acid ester

The sorbitol fatty acid ester preferably has an esterification percentage in the range of 20% to 40%. Sorbitol has 6 hydroxyl groups in its molecule, and its monoester (having one esterified hydroxyl group; esterification percentage: 17%) is most effective to give the fried foodstuffs having satisfactory flowery coating. However, the monoester per se is sparingly soluble in oils and fats. Therefore, a mixture of 5 to 50 weight % of its diesters and/or higher esters and the remainder of its monoester is advantageously employed.

(2) Sorbitan fatty acid ester

The sorbitan fatty acid ester preferably has an esterification percentage in the range of 20% to 40% (more preferably 20% to 30%). Its diester and higher esters are well soluble in oils and fats. However, if such diester and higher esters are contained in a greater amount in the frying oil or fat, the fried foodstuffs are apt to show unsatisfactory excessive oiliness as well as to deteriorate the flowery coating, taste and crisp. Therefore, the frying oil or fat preferably contains a major amount of a sorbitan fatty acid monoester. The fatty acid moiety of the ester preferably is an unsaturated fatty acid moiety, because the ester having unsaturated fatty acids is well soluble in oils and fats. A sorbitol ester may be mixed with the sorbitan ester. Further, solubility of solbitan fatty acid esters is well improved by addition of a diglyceride.

(3) Polyglycerol fatty acid ester

The polyglycerol fatty acid ester preferably has an esterification percentage in the range of 20% to 75% (more preferably 30% to 55%). Preferably, 50 to 90 weight % (more preferably 70 to 90 weight %) of the constitutional fatty acid moieties of the polyglycerol fatty acid ester are occupied by unsaturated fatty acid moieties. The remainder (not more than 50 weight %, particularly 3 to 20 weight %) is a saturated fatty acid moiety. The constitutional unsaturated and saturated fatty acid moieties both have carbon atoms of not less than 14. Preferred examples of the saturated fatty acid are palmitic acid (16 carbon atoms) and stearic acid (18 carbon atoms). Preferred examples of the unsaturated fatty acid are oleic acid, linoleic acid, and linolenic acid, all having 18 carbon atoms. These fatty acids can be employed in any combinations. Condensation degree, namely, number of glycerol moieties in the polyglycerol moiety, preferably is in the range of 2 to 10. The preferred esters are as follows.

| Polyglycerol | Number of fatty acids attached to polyglycerol |
|---|---|
| Diglycerol | 1–2 |
| Triglycerol | 2–3 |
| Tetraglycerol | 2–4 |
| Pentaglycerol | 2–5 |
| Hexaglycerol | 2–6 |
| Heptaglycerol | 3–6 |
| Octaglycerol | 3–6 |
| Nonaglycerol | 3–7 |
| Decaglycerol | 3–8 |

The polyglycerol fatty acid ester preferably has an HLB value in the range of 3.5 to 8.0 (more preferably 4.5 to 7.0).

Concrete examples of preferably employable polyglycerol fatty acid esters are diglycerol monooleate, triglycerol dioleate, tetraglycerol dioleate, tetraglycerol trioleate, hexaglycerol tetraoleate, hexaglycerol pentaoleate, decaglycerol pentaoleate, and decaglycerol heptaoleate.

(4) Alkylglucoside

The alkyl glycoside preferably is a monoalkylglucoside or a dialkylglucoside. The alkyl group preferably has carbon atoms of 18–22, from the viewpoint of compatibility with oils and fats. Particularly preferred are a monoalkylglycoside having carbon atoms of 18–22 and a dialkylglycoside having carbon atoms of 14–18.

(5) Erythritol fatty acid ester

A preferred erythritol fatty acid ester is the monoester having carbon atoms of 18–22.

(6) Polyoxyethylenesorbitan fatty acid ester

Examples of the polyoxyethylenesorbitan fatty acid esters are polyoxyethylenesorbitan monostearate (Polysorbate 60), polyoxyethylenesorbitan tristearate (Polysorbate 65), and polyoxyethylenesorbitan monooleate (Polysorbate 80). Other known polyoxyethylenesorbitan fatty acid esters such as polyoxyethylenesorbitan monopalmitate are also employable.

(7) Sugar fatty acid ester

The sugar fatty acid ester preferably has an esterification degree in the range of 25% to 75%, more preferably 25% to 60%, and most preferably 25% to 45%. Preferably, more than 50 weight % (more preferably 50 to 95 weight %, most preferably 70 to 90 weight %) of the constitutional fatty acid moieties of the sugar ester are occupied by unsaturated fatty acid moieties. The remainder is a saturated fatty acid moiety. The constitutional unsaturated and saturated fatty acid moieties both have carbon atoms of not less than 14. Preferred examples of the saturated fatty acid are palmitic acid (16 carbon atoms) and stearic acid (18 carbon atoms). Preferred examples of the unsaturated fatty acid are oleic acid, linoleic acid, and linolenic acid, all having 18 carbon atoms. These fatty acids can be employed in any combinations.

Sugar fatty acid ester generally comprises a monoester (esterification number: 1, referred to as SME), a diester (esterification number: 2, referred to as SDE), a triester (esterification number: 3, referred to as STE), and polyesters (esterification number: 4–8, referred to as PTE) in combination. The sugar fatty acid ester to be employed in the invention preferably contains relatively greater amount of the diester (SDE) and triester (STE), because the diester and triester are effective in relatively smaller amounts, in reducing smell of burnt oil in the frying procedure and in improving taste and flowery coating of the fried foodstuffs. Accordingly, the sugar fatty acid ester preferably contains the diester (SDE) in an amount of 20–95 wt. % (more preferably 33–90 wt. %) and the triester (STE) in an amount of 15–45 wt. %. Moreover, the total amount of SDE and STE in the oil composition preferably is not less than 0.02 weight %, more preferably 0.05–1.5 weight %. The content of the polyester (SPE, particularly those having esterification number 5 or more) in the sugar ester preferably is not more than 3 weight %, more preferably not more than 1 weight %, because the polyester gives excessive oily taste in a larger amount. Preferred relationship of the contents of these esters are as follows:

([STE]+[SPE])/[SDE]≦4.0

The content of the monoester (SME) in the sugar ester preferably is not more than 10 weight % (more preferably 0.01 to 5 weight %), because a larger content of SME deteriorates the taste of the resulting oil or fat composition and reduces solubility of the sugar ester in oils or fats. The content of SME in the oil or fat composition preferably is not more than 0.1 weight %.

The sugar fatty acid ester can be prepared by known synthesis processes. Generally, a sugar fatty acid ester can be prepared by esterification reaction between sugar and a fatty acid methylester. In more detail, sugar and a fatty acid methylester can be heated under reduced pressure to react in a solvent such as dimethylformamide in the presence of potassium carbonate (catalyst). The esterification reaction is also carreid out in an aqueous solution containing a large amount of an emulsifier. In the aqueous solution, the sugar and fatty acid methylester are heated to give a microemulsion and, after evaporation of water under reduced pressure, the reaction is caused using potassium carbonate as catalyst. Alternatively, sugar and glyceride can directly react with each other using potassium carbonate as catalyst. The resulting reaction mixture is treated to remove excessive sugar and solvent and then partitioned by silica gel column chromatography using chloroform-methanol as eluent to give various fractions. Some of the obtained various fractions are then mixed to give a sugar fatty acid ester having the desired composition, which is favorably used in the invention. The sugar fatty acid ester farborably employed can be obtained by partitioning a commercially available sugar fatty acid ester and appropriately mixing the partitioned fractions. Otherwise, a commercially available sugar fatty acid ester is dissolved in hexane, and to the hexane solution are added ethanol and water in controlled amounts to keep the triester and higher esters in the hexane phase.

The preferred sugar fatty acid ester has the following composition:

2≦mean esterification value≦4.5

([SPE]+[STE])/[SDE]≦2.3

[SME]/[SDE]≦0.1

[SPE]/[SDE]≦0.8

The frying oil or fat composition preferably further contains 5 to 50 weight % (more preferably, 5 to 20 weight %, most preferably 7 to 15 weight %) of a diglyceride so as to prevent production of cloudy insolubles in the oil or fat composition in its storage particularly at lower temperatures.

Some oils and fats of natural origin contain a small amount of diglyceride. However, most of untreated natural oil and fat contain only a negligible amount of diglyceride. Accordingly, the diglyceride can be introduced into the frying oil or fat composition in the form of a diglyceride-rich glyceride mixture. The glyceride mixture preferably contains diglyceride of not less than 50 weight %, more preferably not less than 65 weight %. Other glycerides than the diglyceride in the glyceride mixture are monoglyceride and triglyceride. The amount of monoglyceride preferably is less than 20 weight % of diglyceride. The fatty acid moieties constituting the glyceride are preferably derived from fatty acids of 8–24 carbon atoms. Preferably, not less than 70 weight %, more preferably not less than 80 weight %, of the fatty acids are unsaturated fatty acids. Particularly preferred diglyceride is rich in unsaturated fatty acid moieties.

The diglyceride-rich glyceride mixture can be produced by transesterification between one or more of unsaturated fatty acid-rich oils such as safflower oil, olive oil, cottonseed oil, corn oil, rapeseed oil, soybean oil, palm oil, sunflower oil, sesame oil, lard, beef tallow, fish oil, milk fat, or their fractioned oils, random interesterified oils, hardened oils and transesterified oils, and glycerol in the presence of a hydroxide of an alkali metal or alkaline earth metal. Alternatively, the unsaturated fatty acids and glycerol are caused to undergo transesterification to give a diglyceride-rich glyceride mixture. The obtained diglyceride-rich glyceride mixture can be mixed with the unsaturated fatty acid-rich oil. The produced excessive monoglyceride can be removed by molecular distillation or chromatography. These reactions can be carried out using an alklaine catalyst (that is, chemical synthesis). However, enzymic synthesis using an enzyme such as 1,3-selective lipase under milder conditions is preferably employed, because such diglyceride-rich glyceride mixture prepared under milder conditions effect favorably on the taste of the frying oil or fat composition.

REFERENCE EXAMPLE 1

Dynamic interfacial tensions of various vegetable oils, and their workability in the procedures for frying foodstuffs, as well as characteristics (appearance of flowery coating, and crisp) of the fried foodstuffs were examined. The coating was prepared using a mixture of water, wheat flour, and egg (150:100:50, by weight).

The results are set forth in Table 1.

TABLE 1

| Sample Oil | Dynamic Interfacial Tension (mN/m, 80° C.) | | Frying Workability | | | Fried Foodstuffs | |
|---|---|---|---|---|---|---|---|
| | 3 sec. | 5 sec. | Foam | Smoke | Stain | Coating | Crisp |
| Soybean | >28 | 26 | AA | AA | AA | CC | BB |
| Rapeseed | >28 | >28 | AA | AA | AA | CC | BB |
| Corn | >28 | 27 | AA | AA | AA | CC | BB |
| Rice Bran | 27 | 26 | AA | AA | AA | CC | BB |
| Safflower | >28 | >28 | AA | AA | AA | CC | BB |
| Sunflower | 28 | 27 | AA | AA | AA | CC | BB |

TABLE 1-continued

| Sample Oil | Dynamic Interfacial Tension (mN/m, 80° C.) | | Frying | | | Fried Foodstuffs | |
|---|---|---|---|---|---|---|---|
| | 3 sec. | 5 sec. | Workability | | | Coating | Crisp |
| | | | Foam | Smoke | Stain | | |
| Cottonseed | 28 | 25 | AA | AA | AA | CC | BB |
| Olive | >28 | 28 | AA | AA | AA | CC | BB |
| Sesame | 21 | 19 | AA | BB | BB | CC | BB |

In Table 1, the marks mean the following:

Foam: AA (Almost no foaming is observed)

Smoke: AA (Almost no smoking is observed)

BB (Slight smoking is observed)

Stain: AA (Almost no oil stain by spattering is observed)

BB (Slight oil spattering is observed)

Coating: CC (poor flowery coating is formed)

Crisp: BB (Fried foodstuffs are not crisp, and become sticky upon storage)

The dynamic interfacial tension was measured at 80° C. by the following method.

The sample oil (20 mL) was placed in a cell of Drop Volume Tensiometer-TVT1 (available from LAUDA DR. R. WOBSER GMBH & CO. KG.). Into the cell was dropped a distilled water from a syringe. The interfacial tension was determined from the volume of the dropped water, the outer diameter of the syringe, and a correction factor ($\sigma$=62.60 mN/m, see "Handbook of Chemistry, Fundamental II, 2nd revision" edited by The Chemical Society of Japan",—6.6. Surface Tension and Wetting—). The dynamic interfacial tension (i.e., change of interfacial tension with time) was determined by changing the rate of water dropping from the syringe. In the measurement, a small amount (5 mL) of distilled water was previously charged in the apparatus for performing the measurement at saturated vapor pressure. The measurement error in the use of distilled water at 80° C. was within 1%. The distilled water was prepared by redistilling a commercially available distilled water (available from Wako Junyaku Co., Ltd., Japan). The syringe was a gas tight syringe (5 mL volume, available from Hamilton Corp.). The temperature was controlled using a constant temperature jacket of polycarbonate resin. The temperature control of the glass cell was performed using a constant temperature jacket attached to the above measuring apparatus (TVT1).

EXAMPLE 1

A base oil (corn oil) was mixed with an emulsifier set forth in Table 2 to prepare a frying oil composition (A–H) according to the invention. The corn oil used had the following ingredients: fatty acid 0.4 wt. %; monoglyceride 0.2 wt. %; diglyceride 2.4 wt. %; triglyceride 97.0 wt. %.

The prepared frying oil composition was measured by the aforementioned method to determine its dynamic interfacial tension. The results are set forth in Table 2.

TABLE 2

| | Amount (wt. %) | Sample No. | Interfacial Tension | |
|---|---|---|---|---|
| | | | 3 sec. | 5 sec. |
| Diglycerol monooleate | 0.5 | A1 | 4.2 mN/m | 4.0 mN/m |
| (Mean Esterification Degree: 32%) | 1.0 | A2 | 2.8 | 2.5 |
| Hexaglycerol pentaoleate (M.E.D.: 71%) | 1.0 | B1 | 4.5 | 3.2 |
| | 3.0 | B2 | 1.8 | 1.5 |
| Alkylglucoside (M.E.D.: 20%) | 1.0 | C1 | 2.5 | 2.1 |
| Sorbitol monoester (M.E.D.: 20%) | 0.2 | D1 | 5.0 | 4.2 |
| | 1.0 | D2 | 1.5 | 1.2 |
| Pentaerythritol monoester (M.E.D.: 25%) | 1.0 | E1 | 1.5 | 1.1 |
| Polyoxyethylene sorbitan monostearate (M.E.D.: 35%) | 0.2 | F1 | 2.7 | 1.8 |
| Polyoxyethylene sorbitan trioleate (M.E.D.: 60%) | 0.3 | G1 | 4.5 | 4.0 |
| Sorbitan monoester (M.E.D.: 35%) | 0.5 | H1 | 4.3 | 4.0 |
| | 1.0 | H2 | 3.0 | 2.8 |

Remarks:
Interfacial Tension: Dynamic interfacial tension (at 80° C.)
Diglycerol monooleate: DGMO-90 (Nikko Chemicals Co., Ltd., Japan)
Hexaglycerol monooleate: PO-500 (Sakamoto Chemicals Co., Ltd., Japan)
Alkylglucoside: monoalkylglucoside (fatty acid: oleic acid)
Sorbitol monoester: ester composition (monoester 60 wt. %; diester 28 wt. %; triester 12 wt. %), fatty acids (oleic acid 68 wt. %; palmitic acid 4 wt. %; linoleic acid 11 wt. %; stearic acid 8 wt. %; others 9 wt. %)
Pentaerythritol monoester: ester composition (monoester 54 wt. %; diester 32 wt. %; triester 14 wt. %)
Polyoxyethylene sorbitan monostearate: Tween 60
Polyoxyethylene sorbitan trioleate: Tween 85

The above frying oil compositions were examined in their characteristics in frying procedure, and conditions of flowery coating, crisp and oiliness in taste of the fried foodstuffs. The same corn oil employed for preparing the frying oil composition but containing no emulsifier was also examined as control. The coating was prepared using a mixture of water, wheat flour, and egg (150:100:50, by weight).

The conditions of flowery coating, crisp and oiliness in taste of the fried foodstuffs were evaluated in the following manner.

(1) Evaluation of flowery coating

The test sample (oil composition or oil) was placed in a glass beaker and kept at 180° C. in a heated oil bath. Into the heated sample was dropped the aqueous flour mixture for preparing the coating from a syringe to prepare a flowery fried mass. The dimensions (circumferential length and area) of the fried mass were measured on a photograph of the fried mass. These dimensions were then converted to a shape coefficient (=(circumferential length)$^2$/4$\pi$×area). In each test sample, 50 flowery fried masses were produced, and all of them were measured to give the shape coefficient. The evaluation was then performed by obtaining a mean value of the resulting shape coefficients. The mean values were classified into the following: a group of small values (corresponding to almost round shape with little flowery coating; shape coefficient=1–1.5, 1.5 not inclusive) was allotted 1, and groups of increased values were allotted 2 (with some flowery coating; shape coefficient=1.5–2, 2 not inclusive), 3 (moderate flowery coating; shape coefficient= 2–3, 3 not inclusive), 4 (well acceptable flowery coating; shape coefficient=3–4, 4 not inclusive), and 5 (admirable flower coating; shape coefficient=4 or more).

(2) Crisp and Oiliness in taste

A shrimp was coated with the above-mentioned aqueous flour mixture and fried in the sample oil or oil composition at 180° C. The fried shrimps were taken by a panel of five members. Each member gave his points in the crisp and oiliness in taste in question, according to the criteria of 1 to 5, wherein 1 meant the worst and 5 meant the best. Mean values of the points are set forth in Table 3.

TABLE 3

| Sample Composition | Frying Workability | | | Fried Foodstuffs | | |
| --- | --- | --- | --- | --- | --- | --- |
| | Foam | Smoke | Stain | Coating | Crisp | Oiliness |
| Corn Oil (control) | AA | AA | AA | 1.0 | 2.0 | 3.0 |
| A1 | AA | AA | AA | 3.8 | 4.0 | 4.5 |
| A2 | AA | AA | AA | 4.3 | 4.0 | 3.5 |
| B1 | AA | AA | AA | 2.3 | 3.5 | 4.5 |
| B2 | AA | AA | AA | 4.0 | 4.0 | 3.0 |
| C1 | AA | AA | AA | 3.7 | 4.0 | 5.0 |
| D1 | AA | AA | AA | 1.6 | 3.5 | 4.5 |
| D2 | AA | AA | AA | 3.8 | 4.0 | 4.5 |
| E1 | AA | AA | AA | 4.0 | 4.0 | 3.5 |
| F1 | AA | AA | AA | 4.1 | 4.0 | 4.0 |
| G1 | AA | AA | AA | 4.1 | 4.0 | 3.5 |
| H1 | AA | AA | AA | 3.9 | 3.5 | 4.0 |
| H2 | AA | AA | AA | 4.0 | 4.0 | 3.5 |

As is apparent from the results in Table 3, the fried foodstuffs obtained using the oil composition of the invention having a dynamic interfacial tension below the specific value showed satisfactorily flowery coating, good crisp and well acceptable oiliness in taste.

COMPARISON EXAMPLE 1

A base oil (corn oil) equivalent to the base oil used in Example 1 was mixed with an emulsifier set forth in Table 4 to prepare a frying oil composition (I–L) for comparison.

The prepared frying oil composition was measured by the aforementioned method to determine its dynamic interfacial tension. The results are set forth in Table 4.

TABLE 4

| | Amount (wt. %) | Sample No. | Interfacial Tension | |
| --- | --- | --- | --- | --- |
| | | | 3 sec. | 5 sec. |
| Diglycerol trioleate (Mean Esterification Degree: 68%) | 10.0 | I1 | 25.0 mN/m | 23.0 mN/m |
| Hexaglycerol mixed fatty acid ester (M.E.D.: 88%) | 1.0 | J1 | 25.5 | 24.5 |
| | 5.0 | J2 | 14.7 | 13.5 |
| Decaglycerol decaoleate (M.E.D.: 83%) | 1.0 | K1 | 19.5 | 18.0 |
| | 5.0 | K2 | 14.7 | 13.8 |
| Oleic acid monoglyceride (M.E.D.: 34%) | 3.0 | L1 | 9.2 | 8.7 |
| | 10.0 | L2 | 2.9 | 2.9 |

Remarks:
Interfacial Tension: Dynamic interfacial tension (at 80° C.)
Hexaglycerol mixed fatty acid ester: Ester of hexaglycerol with a mixture of stearic acid and palmitic acid The above frying oil compositions were examined in their characteristics in frying procedure, and conditions of flowery coating, crisp and oiliness in taste of the fried foodstuffs, in the aforementioned manner. The results are set forth in Table 5.

TABLE 5

| Sample Composition | Frying Workability | | | Fried Foodstuffs | | |
| --- | --- | --- | --- | --- | --- | --- |
| | Foam | Smoke | Stain | Coating | Crisp | Oiliness |
| I1 | AA | AA | AA | 1.3 | 2.0 | 1.0 |
| J1 | AA | AA | AA | 1.1 | 2.0 | 2.5 |
| J2 | AA | AA | AA | 1.2 | 2.0 | 1.0 |
| K1 | AA | AA | AA | 1.1 | 1.0 | 2.5 |
| K2 | AA | AA | AA | 1.3 | 1.0 | 1.0 |
| L1 | AA | AA | AA | 1.1 | 2.0 | 1.5 |
| L2 | AA | AA | AA | 2.8 | 4.0 | 1.0 |

As is apparent from the results in Table 5, the fried foodstuffs obtained using the oil composition which contain polyalcohol-type nonoionic surfactant under conditions of not satisfying the conditions of the invention did not show satisfactory characteristics.

EXAMPLE 2

Pieces (thickness: 1.5 cm) of pork were coated with wheat flour, egg and bead crumbs, and fried in the aforementioned oil compositions of A1, B1, and D2 (prepared in Example 1 and according to the invention), respectively, at 180° C.

The conditions (spattering of oil, and smell of deteriorated oil) in the frying procedure were evaluated by a panel of five members. The fried porks were taken by a panel of five members. Each member gave his points in the taste, crisp, and oiliness in taste in question, according to the aforementioned criteria of 1 to 5, wherein 1 meant the worst and 5 meant the best. Mean values of the points are set forth in Table 6.

COMPARISON EXAMPLE 2

Pieces of pork were coated with wheat flour, egg and bead crumbs, and fried in the aforementioned oil compositions of I1 and L2 (prepared in Comparison Example 1), and corn oil, respectively, in the same manner as in Example 2.

The conditions (spattering of oil, and smell of deteriorated oil) in the frying procedure as well as the characteristics of the fried porks were evaluated in the same manner. Mean values of the points are set forth in Table 6.

| Sample Composition | Frying Workability | | Fried Foodstuffs | | |
| --- | --- | --- | --- | --- | --- |
| | Spattering | Smell | Taste | Crisp | Oiliness |
| Invention | | | | | |
| A1 | 4.0 | 4.0 | 4.0 | 4.0 | 4.5 |
| B1 | 4.5 | 5.0 | 4.0 | 3.5 | 4.5 |
| D2 | 4.0 | 3.0 | 4.0 | 3.5 | 4.5 |
| Comparison | | | | | |
| Corn Oil (control) | 2.0 | 2.0 | 3.0 | 3.0 | 2.0 |
| I1 | 2.0 | 2.0 | 1.0 | 1.0 | 1.0 |
| L2 | 4.0 | 1.0 | 1.0 | 1.0 | 4.0 |

As is clear from the results in Table 6, the fried foodstuffs obtained using a simple oil with no emusifier or the oil composition which contain a polyalcohol-type nonoionic surfactant under conditions of not satisfying the conditions of the invention did not show satisfactorily characteristics.

EXAMPLE 3

The oil compositions A1, B1 and D2 according to the invention which were prepared in Example 1 were quantitatively examined in resistance to oxidation in the following manner.

Forty pieces (each 2 cm×5 cm) of filter paper were coated with the aqueous flour mixture prepared in Example 1. These pieces were successively fried in 600 g of the oil composition (or corn oil as control) at 180° C. The used oil was examined in the production of acrolein (oxidation product of oil) as well as COV value (meaning degree of oil oxidation; high COV value means development of oxidation and excessive oiliness). The results are set forth in Table 7.

COMPARISON EXAMPLE 3

The oil compositions I1 and L2 for comparison which was prepared in Comparison Example 1 were quantitatively examined in resistance to oxidation in the same manner as in Example 3. The results are set forth in Table 7.

TABLE 7

| Sample Composition | Emulsifier Compound | Amount (wt. %) | Deterioration of Oil COV | Acrolein |
|---|---|---|---|---|
| Invention | | | | |
| A1 | Diglycerol monooleate | 0.3 | 37 | 2.2 ppm |
| B1 | Hexaglycerol monooleate | 1.0 | 36 | 2.0 ppm |
| D2 | Sorbitol monoester | 1.0 | 38 | 2.7 ppm |
| Comparison | | | | |
| Corn oil (Control) | — | — | 42 | 4.4 ppm |
| I1 | Diglycerol trioleate | 3.0 | 40 | 4.6 ppm |
| L2 | Oleic acid monoglyceride | 10.0 | 45 | 3.9 ppm |

As is apparent from the results seen in Table 7, the oil composition according to the invention is more resistant to oxidation in the frying procedure than the control oil and comparison oil composition.

EXAMPLE 4

The diglycerol monooleate (DGMO-90) described in Example 1 was added at 0.5 weight % to each of other base oils set forth in Table 8. The frying procedure of Example 1 was carried out using the obtained oil composition. The results are set forth in Table 8.

TABLE 8

| Base Oil | Dynamic Interfacial Tension (mN/m, 80° C.) | | Frying Workability | | Fried Foodstuffs | |
|---|---|---|---|---|---|---|
| | 3 sec. | 5 sec. | Foam | Smoke | Coating | Crisp |
| Soybean | 4.3 | 4.0 | AA | AA | BB | BB |
| Rapeseed | 4.2 | 4.0 | AA | AA | BB | BB |
| Corn | 4.2 | 4.0 | AA | AA | BB | BB |
| Sesame | 3.9 | 3.5 | AA | BB | BB | AA |

The marks in Table 8 mean the following:
Foam: AA (Almost no foaming is observed)
Smoke: AA (Almost no smoking is observed)
BB (Slight smoking is observed)
Coating: BB (Well acceptable flowery coating is formed)
Crisp: AA (Satisfactory crisp is noted)
BB (Acceptable crisp is noted)

EXAMPLE 5

In the manner as described in Example 2, a combination of a sugar fatty acid ester and each of other emulsifier was examined in its effect observed in frying pieces of pork. The base oil was corn oil. The sugar fatty acid ester had the following composition:

| | SME | SDE | STE | PTE |
|---|---|---|---|---|
| Sugar Ester A | 1.2% | 38.5% | 42.0% | 10.3% |
| Sugar Ester B | 0.3% | 2.5% | 8.7% | 88.3% |

(SME: monoester, SDE: diester, STE: triester, PTE: polyester (tetraester or higher esters), "%" means "weight %")

The determined dynamic interfacial tension (at 80° C.) is set forth in Table 9. The workability in the frying procedure and the characteristics of the fried pork are set forth in Table 10.

TABLE 9

| | Amount (wt. %) | Sample No. | Sugar ester (wt. %) | Interfacial Tension | |
|---|---|---|---|---|---|
| | | | | 3 sec. | 5 sec. |
| Sorbitol monoester | 0.05 | M1 | A (0.05) | 4.5 mN/m | 3.2 mN/m |
| Sorbitol monoester | 0.08 | M2 | B (1.0) | 4.7 | 4.0 |
| Pentaerythritol monoester | 0.06 | N1 | A (0.05) | 6.0 | 4.3 |
| Alkyl-glucoside | 0.05 | P1 | A (0.05) | 3.7 | 2.6 |
| Alkyl-glucoside | 0.05 | P2 | B (1.0) | 4.4 | 4.0 |

TABLE 10

| Sample Composition | Frying Workability | | Fried Foodstuffs | | |
|---|---|---|---|---|---|
| | Spattering | Smell | Taste | Oiliness | Crisp |
| M1 | 3.8 | 3.8 | 4.5 | 4.5 | 4.2 |
| M2 | 4.0 | 4.0 | 4.0 | 4.0 | 3.8 |
| N1 | 3.6 | 3.8 | 4.0 | 4.4 | 4.0 |

TABLE 10-continued

| Sample Composition | Frying Workability | | Fried Foodstuffs | | |
|---|---|---|---|---|---|
| | Spattering | Smell | Taste | Oiliness | Crisp |
| P1 | 3.5 | 3.6 | 4.0 | 4.4 | 4.2 |
| P2 | 3.8 | 3.6 | 3.8 | 4.4 | 4.0 |

From the results in Tables 9 and 10, it is apparent that a sugar fatty acid ester when used in combination with other emulsifiers reduces an amount of the other emulsifier required to give the lower dynamic interfacial tension as well as to improve the frying workability and various characteristics of the fried foodstuffs.

The following Examples 6 and 7 show the effect of the combination of a sugar fatty acid ester and polyglycerol fatty acid ester in the frying oil composition.

EXAMPLE 6

Preparation of Sugar fatty acid esters A to D

A commercially available sugar fatty acid ester, various fractions obtained by partitioning a commercially available sugar fatty acid ester on silica gel column (eluent: chloroform-methanol) and a sugar ester synthesized from a fatty acid methylester and sugar were appropriately mixed to give the following sugar fatty acid esters A to D.

TABLE 11

| Sugar ester | Ester composition (wt. %) | | | | Ester. Percent. | Fatty acids (%) | | | |
|---|---|---|---|---|---|---|---|---|---|
| | [SME] | [SDE] | [STE] | [SPE] | | O | S + P | L | Etc |
| A | 2.5 | 8.2 | 18.3 | 71.0 | 54 | 73 | 6 | 4 | 17 |
| B | 2.8 | 32.0 | 36.0 | 29.2 | 36.5 | 73 | 6 | 4 | 17 |
| C | 1.5 | 35.0 | 39.0 | 24.5 | 35.8 | 82 | 18 | 8 | 2 |
| D | 1.2 | 38.5 | 42.0 | 10.3 | 30.5 | 82 | 18 | 8 | 2 |

Remarks: "Ester. Percent." means esterification percentage (%). Fatty acids (%) means fatty acid compositions and weight % thereof, wherein "O" stands for oleic acid, "S + P" stands for a composition of stearic acid and palmitic acid, "L" stands for linoleic acid, and "Etc" stands for other fatty acids.

Preparation of polyglycerol fatty acid esters Q to U

One weight part of hexaglycerol and 3.3 weight parts of oleic acid (purity: 76%) were mixed and reacted at 200° C. under a nitrogen gas stream in the presence of sodium hydroxide (catalyst). After the reaction was complete, the reaction mixture was allowed to stand for separating the desired hexaglycerol pentaoleate. If necessary, the reaction mixture was treated with active carbon and/or clay. An appropriate polyglycerol and oleic acid were also reacted in the same manner except that the ratio of the glycerol and oleic acid was varied and the reaction temperature was controlled to give various polyglycerol oleic acid esters (PGE) Q to U. The obtained polyglycerol oleic acid esters are set forth in Table 12.

TABLE 12

| PGE | Composition | Ester. Percentage | HLB |
|---|---|---|---|
| P | Diglycerol monooleate (DGMO-90, Nikko Chemicals) | approx. 20% | 6.5 |
| Q | Hexaglycerol pentaoleate | approx. 67% | 4.2 |
| R | Hexaglycerol trioleate | approx. 38% | 6.6 |
| S | Hexaglycerol tetraoleate | approx. 53% | 5.2 |
| T | Decaglycerol pentaoleate | approx. 40% | 6.4 |
| U | Decaglycerol heptaoleate | approx. 62% | 4.9 |

Preparation of Oil composition I (of the invention)

To 800 g of a commercial available corn salad oil (produced by Ajinomoto Ltd., Japan), the sugar fatty acid ester A and the polyglycerol fatty acid ester Q (hexaglycerol pentaoleate) were so added that the contents of the sugar acid A and polyglycerol ester Q in the oil composition were 0.2 weight % and 0.05 weight %, respectively. Thus, Oil composition I according to the invention was prepared.

Preparation of Oil compositions II–XI (of the invention)

Oil compositions II to XI according to the invention were prepared in the same manner as above, except that the sugar fatty acid ester and polyglycerol fatty acid ester and their amounts were varied as set forth in Table 13.

Preparation of Oil compositions a to c (for comparison)

Oil compositions a to c for comparison were prepared in the same manner as in the preparation of Oil composition I, except that the sugar fatty acid ester of the kind and amount set forth in Table 13 only was used.

Preparation of Oil compositions p to q-1 (for comparison)

Oil compositions p to q-1 for comparison were prepared in the same manner as in the preparation of Oil composition I, except that the polyglycerol fatty acid ester of the kind and amount set forth in Table 13 only was used.

Evaluation of Oil Composition

The flowery coating, taste of fried foodstuffs, production of mal odor by heating (smell of deteriorated oil), and crisp of fried foodstuffs were evaluated using the above-prepared oil compositions.

Test method

Five pieces of sweet potatoes (in the form of disk, diameter 3 cm, height 0.5 cm, weight 3 g) were coated with an aqueous flour dough (egg/water/flour having low gluten content=one egg/150 g/100 g, mixed at 0° C.).

In 500 g of the oil composition heated to 200° C. in iron-made frying pot (diameter 15 cm, height 8 cm) were placed the above coated five sweet potatoes, and after 4 minutes the fried sweet potatoes were taken out of the oil.

Evaluation of flowery coating

The flower coating was evaluated in the manner as described in Example 1.

Evaluation of mal odor of heated oil (burning smell)

Forty pieces of filter papers were fried in the manner as described in Example 3. The odor produced from the fried filter paper was ranked by a panel of plural members in the follwing manner:

Mark 1 is given when mal odor is produced as that in the use of a commercially available corn salad oil, and Mark 5 is given when no mal odor is produced. Marks 2, 3 and 4 are given to the intermediate levels of mal odor, in order. Finally, these marks are processed to give an average value.

Evaluation of taste of fried foodstuffs

The sweet potatos fried in a corn oil and those fried in each of the oil composition were compared by a panel of plural members. The ranking of five levels was made according to the following criteria:

Mark 1 is given when the sweet potatos fried in a corn oil is prominently better than those fried in the oil composition in their taste; Mark 3 is given when there is no noticed significant difference between the sweet potatos fried in a corn oil and those fried in the oil composition; and Mark 5 is given when the sweet potatos fried in the oil composition is prominently better than those fried in a corn oil.

Evaluation of crisp of fried foodstuffs

Shrimps and leaves of beefsteak plant coated with the dough were fried at 180° C. in an oil composition of the invention, as well as in a corn salad oil. The fried shrimps and leaves were allowed to stand for 5 min., and taken by a panel of plural members for giving their rank on the crisp of the fried foodstuffs according to the following criteria:

5: The coating of the foodstuffs fried in the oil composition gives prominently better crisp than that of the foodstuffs fried in a corn oil;

4: The coating of the foodstuffs fried in the oil composition gives somewhat better crisp than that of the foodstuffs fried in a corn oil;

3: There is noticed no difference in crisp between coating of the foodstuffs fried in the oil composition and that of the foodstuffs fried in a corn oil;

2: The coating of the foodstuffs fried in a corn oil gives somewhat better crisp than that of the foodstuffs fried in the oil composition; and 1: The coating of the foodstuffs fried in a corn oil gives distinctly better crisp than that of the foodstuffs fried in the oil composition.

The results are set forth in Table 13.

TABLE 13

| Oil Comp. | Sugar ester | Amount (%) | Polygly. ester | Amount (%) | Crisp | Taste | odor | Coating |
|---|---|---|---|---|---|---|---|---|
| Invention | | | | | | | | |
| I | A | 0.2 | Q | 0.05 | 3.8 | 3.2 | 3.0 | 4 |
| II | B | 0.1 | P | 0.02 | 3.5 | 4.4 | 4.5 | 4 |
| III | C | 0.1 | Q | 0.05 | 3.5 | 4.4 | 4.4 | 4 |
| IV | B | 0.2 | Q | 0.05 | 4.5 | 4.4 | 4.6 | 5 |
| V | B | 0.2 | P | 0.02 | 4.2 | 4.4 | 4.0 | 5 |
| VI | C | 0.2 | Q | 0.04 | 4.6 | 4.4 | 4.4 | 5 |
| VII | D | 0.18 | R | 0.12 | 4.0 | 3.8 | 3.8 | 4 |
| VIII | D | 0.18 | T | 0.12 | 3.8 | 4.0 | 4.0 | 5 |
| IX | D | 0.18 | S | 0.12 | 3.8 | 4.2 | 4.2 | 4 |
| X | D | 0.18 | U | 0.1 | 3.8 | 4.0 | 3.6 | 4 |
| XI | D | 0.18 | Q | 0.12 | 3.8 | 4.0 | 3.6 | 5 |
| Comparison | | | | | | | | |
| a | A | 0.1 | — | — | 1.0 | 3.0 | 2.0 | 1 |
| b | B | 0.1 | — | — | 2.0 | 3.6 | 2.0 | 2 |
| c | C | 0.6 | — | — | 4.5 | 2.4 | 3.5 | 5 |
| p | — | — | P | 0.2 | 2.4 | 2.0 | 3.0 | 3 |
| q | — | — | Q | 0.1 | 2.0 | 3.0 | 3.0 | 1 |
| q-1 | — | — | Q | 0.5 | 4.0 | 3.0 | 2.0 | 3 |

Apparently, the oil compositions according to the invention give well ballanced characteristics to the fried foodstuffs in taste, crisp, odor and flowery coating.

EXAMPLE 7

Using commercially available immobilized 1,3-selective lipase reagent (Lypozyme 3A, available from Novo Industry A.S.) as catalyst, 860 g of a fatty acid derived from rapeseed oil) and 140 g of glycerol were reacted at 40° C. After the reaction was complete, the lipase reagent was filtered off, and the reaction product was purified by molecuar distillation, to give a glyceride mixture comprising 80 wt. % of a diglyceride, 18 wt. % of triglyceride, and 2 wt. % of monoglyceride. The fatty acid moieties comprised 78 wt. % of $C_{18}$ unsaturated fatty acid, 2 wt. % of $C_{20}$ unsaturated fatty acid, and 20 wt. % of $C_{14}$–$C_{18}$ saturated fatty acids.

Preparation of Oil compositions I-1 to VII-1 (Invention)

Glyceride mixtures were prepared by addition of 10 weight % of the above-obtained diglyceride-rich composition to the oil compositions I to VII described in Example 6. Thus, the oil compositions I-1 to VII-1 according to the invention were prepared.

Test for Storage Stability

The oil compositions I to VII described in Example 6 and the above oil compositions I-1 to VII-1 were tested in their storage stability in the following manner.

The oil composition was kept at 40° C., 70% RH to reach its water content of 800 ppm, and thus prepared oil composition was kept in a sealed container at 5° C. for one week.

The oil composition was then observed and marked according to the following criteria:

5: Clear with no fog
4: Clear with slight fog
3: Foggy
2: Turbid and Foggy
1: Precipitation observed The results are set forth in Table 14.

TABLE 14

| Oil Comp. | Sugar ester | Amount (%) | Polygly. ester | Amount (%) | Diglyceride Amount (%) | Mark |
|---|---|---|---|---|---|---|
| Invention | | | | | | |
| I-1 | A | 0.2 | Q | 0.05 | 10.0 | 5.0 |
| I | A | 0.2 | Q | 0.05 | — | 4.0 |
| II-I | B | 0.1 | P | 0.02 | 10.0 | 4.5 |
| II | B | 0.1 | P | 0.02 | — | 3.0 |
| III-I | C | 0.1 | Q | 0.05 | 10.0 | 5.0 |
| III | C | 0.1 | Q | 0.05 | — | 4.0 |
| IV-1 | B | 0.2 | Q | 0.05 | 10.0 | 5.0 |
| IV | B | 0.2 | Q | 0.05 | — | 4.5 |
| V-1 | B | 0.2 | P | 0.02 | 10.0 | 4.0 |
| V | B | 0.2 | P | 0.02 | — | 3.5 |
| VI-I | C | 0.2 | Q | 0.04 | 10.0 | 5.0 |
| VI | C | 0.2 | Q | 0.04 | — | 4.5 |
| VII-I | D | 0.18 | R | 0.12 | 10.0 | 4.5 |
| VII | D | 0.18 | R | 0.12 | — | 3.0 |

Apparently, the addition of diglyceride to the oil compositions according to the invention improves the storage stability.

EXAMPLE 8

This example shows the effect of the combination of a sugar fatty acid ester and a diglyceride in the frying oil composition.

Preparation of Sugar fatty acid esters E to K

A commercially available sugar fatty acid ester, various fractions obtained by partitioning a commercially available sugar fatty acid ester on silica gel column (eluent: chloroform-methanol) and a sugar ester synthesized from a fatty acid methylester and sugar were appropriately mixed to give the following sugar fatty acid esters E to K.

TABLE 15

| Sugar ester | Ester composition (wt. %) | | | | Ester. Value | Fatty acids (%) | | | |
|---|---|---|---|---|---|---|---|---|---|
| | [SME] | [SDE] | [STE] | [SPE] | | O | S + P | L | Etc |
| E | 2.5 | 8.8 | 20.8 | 67.9 | 4.4 | 70 | 30 | — | — |
| F | 3.1 | 45.4 | 20.0 | 31.5 | 3.6 | 70 | 30 | — | — |
| G | 4.0 | 66.7 | 25.1 | 4.2 | 3.0 | 70 | 30 | — | — |
| H | 2.4 | 70.2 | 9.5 | 17.9 | 2.5 | 70 | 30 | — | — |
| I | 0.5 | 90.8 | 2.3 | 6.4 | 2.3 | 90 | 10 | — | — |
| J | 2.8 | 32.0 | 36.0 | 29.2 | 3.2 | 73 | 10 | 4 | 13 |
| K | 0.5 | 31.5 | 40.4 | 27.6 | 3.2 | 73 | 10 | 4 | 13 |

Remarks: "Ester. Value" means number of fatty acid moieties attached to the sugar moiety. Fatty acids (%) means fatty acid compositions and weight % thereof, wherein "O" stands for oleic acid, "S + P" stands for a composition of stearic acid and palmitic acid, "L" stands for linoleic acid, and "Etc" stands for other fatty acids.

Preparation of Oil composition E-1 (of the invention)

To 800 g of a commercial available corn salad oil (produced by Ajinomoto Ltd., Japan), the sugar fatty acid ester E and the diglyceride mixture prepared in Example 7 were so added that the contents of the sugar acid E and diglyceride in the oil composition were 0.1 weight % and 5 weight %, respectively. Thus, Oil composition E-1 according to the invention was prepared.

Preparation of Oil compositions E-2 to E-4 (of invention)

Oil compositions E-2 to E-4 according to the invention were prepared in the same manner as above, except that the amounts of the sugar fatty acid ester E and diglyceride were varied as set forth in Table 16.

Preparation of Oil compositions r to t (for comparison)

Oil compositions r to t for comparison were prepared in the same manner as in the preparation of Oil composition E-1, except that the content of diglyceride was varied to 5.0 wt. %, 8.0 wt. % and 10.0 wt. %, respectively.

Preparation of Oil compositions E-4 to E-7 (comparison)

Oil compositions E-4 to E-7 for comparison were prepared in the same manner as in the preparation of Oil composition E-1, except that the content of the sugar fatty acid ester E was varied to 0.1 wt. %, 0.15 wt. %, and 0.2 wt. %, respectively.

Evaluation of Foaming of Oil Composition

The production of foam in the frying procedure (i.e., foam stain) was examined twice, namely, after the first frying procedure, and then after the second frying procedure by frying a pair of coated pork slices in the oil composition to be tested. The details of the frying conditions and evaluation method are given below.

Test method

Each of two pork slices (120 g per each) was coated with a mixture of egg (approx. 8 g), flour of lower gluten content (approx. 5 g), and bread crumbs (12 g). The two coated porks were placed in the oil composition heated to 180° C. in a shallow round-bottomed frying pot (diameter: 32 cm). After 4 minutes, the fried two porks were taken out of the oil composition to give fried porks.

In these frying procedures, the foam stain was examined and given a mark according to the following criteria:

5: Foam quickly diminishes in the frying procedure, and no foam remains on the surface of the oil composition.

4: Foam quickly diminishes in the frying procedure, and some foams remain on the surface of the oil composition.

3: Foam slowly diminishes in the frying procedure, and foams remain on an area of one fifth of the surface of the oil composition.

2: Foam very slowly diminishes in the frying procedure, and foams remain on an area of one fourth of the surface of the oil composition.

1: Foaming is marked in the frying procedure, and foams remain on an area of one third of the surface of the oil composition.

For comparison, the same frying procedures were performed using a corn salad oil.

The results are set forth in Table 16.

TABLE 16

| Oil | Diglyceride | Sugar ester | Foaming | |
|---|---|---|---|---|
| Comp. | Amount (%) | Amount (%) | First | Second |
| Invention | | | | |
| E-1 | 5.0 | 0.1 | 4 | 3 |
| E-2 | 5.0 | 0.2 | 4 | 4 |
| E-3 | 7.5 | 0.2 | 5 | 4 |
| E-4 | 7.5 | 0.1 | 5 | 4 |
| Comparison | | | | |
| r | 5.0 | — | 3 | 2 |
| s | 8.0 | — | 3 | 2 |
| t | 10.0 | — | 3 | 3 |
| E-5 | — | 0.1 | 3 | 2 |
| E-6 | — | 0.15 | 3 | 2 |
| E-7 | — | 0.2 | 3 | 3 |
| corn oil | 1.8 | — | 3 | 1 |

Test for Quick Termination of Oil Dripping

Oil compositions XVII to XXII according to the invention were prepared by adding the sugar fatty acid esters E to K, respectively, and the diglyceride mixture to 800 g of commerically available corn salad oil (available from Ajinomoto Ltd.) so that the contents of the sugar fatty acid ester and diglyceride were adjusted to the amounts set forth in Table 17.

Each of eight square pieces (3 cm×3 cm×1 cm) of potato was coated with a dough prepared from approx. 1.5 g of wheat flour, approx. 2 g of egg, and approx. 3 g of bread crumbs. These eight potato pieces were placed in 600 g of the oil composition heated to 180° C. in the shallow, round-bottomed pot at once. After 4 minutes, the fried potatoes were taken out of the oil composition, kept above the surface of the oil composition for 5 seconds, placed on a tray for 5 minutes, and then transferred onto a sheet (diameter: 16 cm) of filter paper. After the fried potatoes were kept on the filter paper sheet for 5 minutes, the oily area of the filter paper sheet was measured to evaluate the quick termination of oil dripping. The evaluation was made using a filter paper sheet on which four fried potato pieces had been placed, according to the following criteria:

5: oily area of 0.0–2.0 cm$^2$

4: oily area of 2.1–5.0 cm$^2$

3: oily area of 5.1–10.0 cm$^2$

2: oily area of 10.1–15.0 cm$^2$

1: oily area of larger than 15.1 cm$^2$

The quick termination of oil dripping was examined twice. Further. the aforementioned foaming test was also carried out.

For comparison, the same frying procedures were performed using a corn salad oil.

The results are set forth in Table 17.

TABLE 17

| Oil | Diglyceride Amount | Sugar ester Amount | Foaming | | Oil Dripping | |
|---|---|---|---|---|---|---|
| Comp. | (%) | (%) | First | Second | First | Second |
| Invention | | | | | | |
| E-5 | 10.0 | 0.2 | 3 | 3 | 2 | 2 |
| F-1 | 10.0 | 0.2 | 5 | 4 | 4 | 3 |
| G-1 | 7.5 | 0.2 | 5 | 4 | 4 | 4 |
| H-1 | 7.5 | 0.2 | 4 | 3 | 4 | 4 |
| I-1 | 10.0 | 0.2 | 5 | 5 | 4 | 4 |
| J-1 | 10.0 | 0.2 | 4 | 4 | 4 | 3 |
| K-1 | 10.0 | 0.2 | 4 | 4 | 4 | 3 |
| Comparison corn oil | 1.8 | — | 3 | 2 | 1 | 1 |

Apparently, the oil compositions containing the sugar fatty acid ester and diglyceride in combination according to the invention give not only low foaming but also quick termination of oil dripping from the fried foodstuffs.

Test for Storage Stability

Preparation of Oil composition E-6 (of the invention)

To 800 g of a commercial available corn salad oil (produced by Ajinomoto Ltd., Japan), the sugar fatty acid ester E and the diglyceride mixture prepared in Example 7 were so added that the contents of the sugar acid E and diglyceride in the oil composition were 0.2 weight % and 10.0 weight %, respectively. Thus, Oil composition E-6 according to the invention was prepared.

Preparation of Oil compositions F-2 to K-2 (of invention)

Oil compositions F-2 to K-2 according to the invention were prepared in the same manner as above, except that the sugar fatty acid ester E was replaced with the sugar fatty acid esters F to K, respectively.

The above-prepared oil compositions were tested in their storage stability in the aforementioned manner.

The results are set forth in Table 18.

TABLE 18

| Oil | Sugar ester | Storage Stability | |
|---|---|---|---|
| Comp. | Amount (%) | No diglyceride | 10 wt % diglyceride |
| Invention | | | |
| E-6 | 0.2 | 4.5 | 5.0 |
| F-1 | 0.2 | 5.0 | 5.0 |
| G-1 | 0.2 | 2.0 | 3.0 |
| H-1 | 0.2 | 3.5 | 4.0 |
| I-1 | 0.2 | 2.5 | 3.5 |
| J-1 | 0.2 | 3.5 | 4.5 |
| K-1 | 0.2 | 4.0 | 5.0 |

Apparently, the oil compositions containing a sugar fatty acid ester and diglyceride in combination according to the invention is improved in the storage stability.

EXAMPLE 9

Preparation of Sugar fatty acid ester mixtures P & Q of the invention and Sugar fatty acid ester mixtures W & X for comparison In a three-necked flask (volume: 1 liter) was placed 75 g of a fatty acid methylester (oleic acid: stearic acid=90:10). To the fatty acid methylester was added at 100° C. with stirring 90 g of sugar. The mixture was then heated to 105°–120° C. for 30 min. with stirring under reduced pressure of 25–50 mmHg to remove produced water. To the reaction mixture were added 2.6 g of potassium carbonate and 7 g of 30 wt. % potassium methylate in methanol. The reaction mixture was again heated to 140°– 160° C. for 8 hours under reduced pressure of 5–10 mmHg, to give a mixture of sugar fatty acid esters. The obtained sugar fatty acid ester mixture was processed on a silica gel column using chloroform/methanol (eluent) to give a various fractions. Some of the obtained fractions were appropriately combined to give the desired sugar fatty acid ester mixtures P and Q of the invention as well as the sugar fatty acid ester mixtures W & X for comparison.

Other sugar fatty acid ester mixtures L, M, N, O, and R according to the invention and sugar fatty acid ester mixtures S, T, U, and V were prepared by mixing the above-obtained fractions.

The compositions of the sugar fatty acid ester mixtures were set forth in Tables 19 and 20.

Evaluation of Sugar fatty acid ester mixture

Preparation of Oil compositions L-1 & L-2 (of invention)

To 500 g of a commerically available corn salad oil (Ajinomoto Ltd.) was added 0.2 weight % or 1.0 weight % of the sugar fatty acid ester L, to give an oil composition L-1 or L-2 according to the invention.

Preparation of Oil compositions S-1 & S-2 (comparison)

To 500 g of a commerically available corn salad oil (Ajinomoto Ltd.) was added 0.2 weight % or 1.0 weight % of the sugar fatty acid ester S, to give an oil composition S-1 or S-2 for comparison.

Preparation of Oil compositions M-1 to R-1 (of invention)

To 500 g of a commerically available corn salad oil (Ajinomoto Ltd.) was added 0.2 weight of one of the sugar fatty acid esters M to R. Thus, oil compositions M-1 to R-1 according to the invention were prepared.

Preparation of Oil compositions T-1 to X-1 (comparison)

TABLE 19

| Sugar ester | Ester composition (wt. %) | | | | Ester. Value | Fatty acids (%) | | |
|---|---|---|---|---|---|---|---|---|
| | [SME] | [SDE] | [STE] | [SPE] | | O | S + P | L |
| Invention | | | | | | | | |
| L | 1.0 | 45.4 | 31.2 | 22.4 | 2.8 | 48.5 | 50.0 | 1.2 |
| M | 1.0 | 76.2 | 22.2 | 10.6 | 2.3 | 48.5 | 50.0 | 1.2 |
| N | 2.4 | 70.2 | 14.4 | 13.0 | 2.4 | 68.2 | 30.0 | 1.8 |
| O | 2.0 | 60.5 | 20.3 | 17.2 | 2.5 | 81.9 | 12.2 | 2.1 |
| P | 2.0 | 38.2 | 35.6 | 24.2 | 2.8 | 81.9 | 12.2 | 2.1 |
| Q | 1.3 | 40.2 | 36.8 | 21.7 | 2.8 | 27.6 | 0.6 | 71.6 |
| R | 3.3 | 35.2 | 38.9 | 22.6 | 2.8 | 26.4 | 0.2 | 73.4 |
| Comparison | | | | | | | | |
| S | 0.5 | 2.9 | 31.2 | 65.4 | 4.9 | 48.5 | 50.0 | 1.2 |
| T | 40.0 | 35.0 | 22.0 | 3.0 | 1.9 | 48.5 | 50.0 | 1.2 |
| U | 5.3 | 11.2 | 27.3 | 56.2 | 4.5 | 68.2 | 30.1 | 1.8 |
| V | 73.1 | 22.6 | 4.3 | 0.0 | 1.3 | 68.2 | 30.0 | 1.8 |
| W | 10.5 | 30.1 | 30.6 | 28.8 | 2.8 | 81.9 | 12.2 | 2.1 |
| X | 19.2 | 27.5 | 32.1 | 21.2 | 2.6 | 81.9 | 21.0 | 2.1 |

Remarks: "Ester. Value" means number of fatty acid moieties attached to the sugar moiety. Fatty acids (%) means fatty acid compositions and weight % thereof, wherein "O" stands for oleic acid, "S + P" stands for a composition of stearic acid and palmitic acid, "L" stands for linoleic acid, and "Etc" stands for other fatty acids.

TABLE 20

| Sugar | ([SPE] + [STE])/[SDE] | [SME]/[SDE] | [SME]/[SDE] |
|---|---|---|---|
| Invention | | | |
| L | 1.18 | 0.02 | 0.49 |
| M | 0.30 | 0.01 | 0.14 |
| N | 0.39 | 0.03 | 0.19 |
| O | 0.62 | 0.03 | 0.28 |
| P | 1.57 | 0.05 | 0.63 |
| Q | 1.46 | 0.03 | 0.54 |
| R | 1.75 | 0.09 | 0.64 |
| Comparison | | | |
| S | 33.1 | 0.17 | 22.55 |
| T | 0.71 | 1.14 | 0.09 |
| U | 7.46 | 0.47 | 5.02 |
| V | 0.19 | 3.23 | 0.00 |
| W | 1.97 | 0.35 | 0.96 |
| X | 1.94 | 0.70 | 0.77 |

To 500 g of a commerically available corn salad oil (Ajinomoto Ltd.) was added 0.2 weight % of one of the sugar fatty acid esters T to X. Thus, oil composition T-1 to X-1 for comparison were prepared.

(1) Solubility in oil (oil solubility)

The above-obtained oil composition was heated at 60° C. for 1 hr. with stirring. After the heating, the oil composition was observed to check presence of insolubles.

(2) Oil spattering

Five disc shaped pieces of pork (each, diameter 3 cm× height 1 cm, weight 9 g) were coated with 20 g of a coating dough (a mixture of one egg, 120 g of water, and 100 g of wheat flour of low gluten content, prepared at 0° C.). These five coated pork pieces were placed in the oil composition heated to 200° C. in an iron-made frying pot (diameter: 15 cm, height: 8 cm). After 4 minutes, the fried pork pieces were taken out of the oil compositions.

A sheet of paper was kept horizontally above the surface of the heated oil composition at a distance of 8 cm during the frying procedure. After the frying procedure, the paper sheet was removed and compared with predetermined five standard paper sheets.

The standard sheet #1 was prepared by the same procedure as above, except for using a base oil (i.e., corn oil) in place of the oil composition. Thus, the standard sheet #1 showed the condition of extremely active spattering. The standard sheet #5 was prepared by the same procedure as that for preparing the standard sheet #1 except for changing the frying temperature from 200° C. to 140° C. Thus, the standard sheet #5 showed the condition of almost no spattering (note that the temperature of 140° C. was too low to prepare acceptable fired foodstuffs.). Each of other standard sheets #2, #3, and #4 was prepared by the same procedure as that for preparing the standard sheet #1 except for adding a certain amount of a surfactant to place thereon the condition of intermediate spattering degree. The degree of spattering increases in order of #4, #3 and #2.

(3) Evaluation of flowery coating

The evaluation was peroformed in the manner described in Example 6.

(4) Evaluation of mal odor of heated oil (burning smell)

The evaluation was peroformed in the manner described in Example 6.

(5) Evaluation of taste of fried foodstuffs

The evaluation was peroformed in the manner described in Example 6.

(6) Evaluation of storage stability

The evaluation was peroformed in the manner described in Example 7.

The results are set forth in Table 21. In Table 21, the values are mean values.

TABLE 21

| Oil Comp. | Sugar ester Amount (%) | Insolubles | Spattering | Coating | Taste | Mal Odor | Storage stability |
| --- | --- | --- | --- | --- | --- | --- | --- |
| Invention | | | | | | | |
| L-1 | 0.2 | None | 3.0 | 3.0 | 3.3 | 3.8 | 5.0 |
| L-2 | 1.0 | None | 4.0 | 4.5 | 3.2 | 3.6 | 5.0 |
| M-1 | 0.2 | None | 3.0 | 4.0 | 4.0 | 3.8 | 5.0 |
| N-1 | 0.2 | None | 4.0 | 4.5 | 4.0 | 3.0 | 4.0 |
| O-1 | 0.2 | None | 3.0 | 4.0 | 4.0 | 3.0 | 4.0 |
| P-1 | 0.2 | None | 2.0 | 3.5 | 3.0 | 3.6 | 4.0 |
| Q-1 | 0.2 | None | 3.0 | 3.5 | 3.0 | 3.0 | 4.5 |
| R-1 | 0.2 | None | 4.0 | 3.5 | 3.0 | 2.6 | 3.0 |
| Comparison | | | | | | | |
| S-1 | 0.2 | None | 1.0 | 1.0 | 3.0 | 3.8 | 5.0 |
| S-2 | 1.0 | None | 2.0 | 1.5 | 2.5 | 3.8 | 5.0 |
| T-1 | 0.2 | Seen | 4.0 | 2.0 | 1.0 | 1.0 | 1.0 |
| U-1 | 0.2 | Seen | 3.5 | 3.0 | 2.0 | 2.6 | 1.0 |
| V-1 | 0.2 | Seen | 4.5 | 2.5 | 1.0 | 1.0 | 1.0 |
| W-1 | 0.2 | Seen | 4.0 | 2.5 | 2.0 | 3.0 | 1.0 |
| X-1 | 0.2 | Seen | 3.0 | 3.0 | 2.0 | 2.6 | 1.0 |

Apparently, the oil compositions containing the sugar fatty acid ester specifically selected according to the invention show well ballanced characteristics in the use as frying oils.

We claim:

1. A frying oil or fat composition consisting essentially of a major portion of an oil or a fat, 0.01–5 weight % of a sugar fatty acid ester, and 0.01–5 weight % of a polyglycerol fatty acid ester.

2. The frying oil or fat composition as defined in claim 1, wherein the sugar fatty acid ester comprises at least 20 weight % of a sugar fatty acid diester and 15–75 weight % of a sugar fatty acid triester.

3. The frying oil or fat composition as defined in claim 1, wherein the sugar fatty acid ester contains not more than 10 weight % of a sugar fatty acid monoester.

4. The frying oil or fat composition as defined in claim 1, wherein the polyglycerol fatty acid ester has an esterification value in the range of 20% to 75%.

5. A frying oil or fat composition comprising a major portion of an oil or a fat, 0.01–5 weight % of a sugar fatty acid ester, and 5 . 50 weight % of a diglyceride.

6. The frying oil or fat composition as defined in claim 5, wherein the sugar fatty acid ester comprises at least 20 weight % of a sugar fatty acid diester and 15–45 weight % of a sugar fatty acid triester.

7. The frying oil or fat composition as defined in claim 5, wherein the sugar fatty acid ester contains not more than 10 weight % of a sugar fatty acid monoester.

8. The frying oil or fat composition as defined in claim 5, wherein the diglyceride has fatty acid moieties, at least 70 wight % of the fatty acid moieties being unsaturated fatty acid moieties.

9. A frying oil or fat composition consisting essentially of a major portion of an oil or a fat and 0.01–5 weight % of a sugar fatty acid ester, in which the sugar fatty acid ester comprises a sugar fatty acid monoester, a sugar fatty acid diester, a sugar fatty acid triester, and a sugar fatty acid polyester comprising its tetra or higher esters, under the following conditions:

$$2 \leq \text{mean esterification value} \leq 4.5$$

$$([SPE]+[STE])/[SDE] \leq 2.3$$

$$[SME]/[SDE] \leq 0.1$$

$$[SPE]/[SDE] \leq 0.8$$

wherein [SME], [SDE], [STE], and [SPE] mean amounts of the sugar fatty acid monoester, sugar fatty acid diester, sugar fatty acid triester, and sugar fatty acid polyester, respectively, comprised in the sugar fatty acid ester.

10. The frying oil or fat composition as defined in claim 9, wherein the sugar fatty acid ester has fatty acid moieties, at least 70 weight % of the fatty acid moieties being unsaturated fatty acid moieties.

11. A frying oil or fat composition which consisting essentially of an oil or fat and an emulsifier, wherein the amount of emulsifier is not greater than 4.0 weight % and is selected from the group consisting of sugar fatty acid esters, sorbitol fatty acid esters, sorbitan fatty acid esters, polyglycerol fatty acid esters, alkylglucosides, erythritol fatty acid esters, and polyoxyethylenesorbitan fatty acid esters, the emulsifier being selected so as to make the oil or fat composition exhibit an interfacial tension of not more than 7 mN/m at 80° C. at a time 3 seconds after the time when the oil or fat composition is mixed with water to form an interface between an oil or fat phase and an aqueous phase.

12. The frying oil or fat composition as defined in claim 11, wherein the emulsifier comprises a combination of a sugar fatty acid ester and a polyalcohol type nonionic surfactant selected from the group consisting of sorbitol fatty acid esters, sorbitan fatty acid esters, alkylglucosides, erythritol fatty acid esters, and polyoxyethylenesorbitan fatty acid esters.

13. The frying oil or fat composition as defined in claim 11, wherein said emulsifier is selected to make the oil or fat composition show an interfacial tension of not more than 5 mN/m at 80° C. at 3 seconds after the formation of the interface.

14. A frying oil or fat composition consisting essentially of a major portion of an oil or fat, 0.01–5 wt. % of sugar fatty acid ester, 0.01–5 wt. % of a polyglycerol fatty acid ester, and 5–50 wt. % of a diglyceride.

* * * * *